(12) United States Patent
Morrissette

(10) Patent No.: US 11,712,263 B2
(45) Date of Patent: Aug. 1, 2023

(54) SURGICAL INSTRUMENT GUIDE

(71) Applicant: Intuitive Surgical Operations, Inc., Sunnyvale, CA (US)

(72) Inventor: Tyler J. Morrissette, Niantic, CT (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1193 days.

(21) Appl. No.: 16/317,392

(22) PCT Filed: Jul. 12, 2017

(86) PCT No.: PCT/US2017/041782
§ 371 (c)(1),
(2) Date: Jan. 11, 2019

(87) PCT Pub. No.: WO2018/013730
PCT Pub. Date: Jan. 18, 2018

(65) Prior Publication Data
US 2021/0275212 A1    Sep. 9, 2021

Related U.S. Application Data

(60) Provisional application No. 62/361,934, filed on Jul. 13, 2016.

(51) Int. Cl.
| | | |
|---|---|---|
| *A61B 17/34* | (2006.01) | |
| *B29C 45/00* | (2006.01) | |
| *B29C 45/26* | (2006.01) | |
| *A61B 17/00* | (2006.01) | |

(52) U.S. Cl.
CPC ...... *A61B 17/3421* (2013.01); *A61B 17/3474* (2013.01); *B29C 45/0001* (2013.01);
(Continued)

(58) Field of Classification Search
CPC .... A61B 2017/3445; A61B 2017/3466; A61B 2017/3449; A61B 17/3421;
(Continued)

(56) References Cited

U.S. PATENT DOCUMENTS

| 5,531,757 A | 7/1996 | Kensey et al. |
|---|---|---|
| 8,622,969 B2 | 1/2014 | Albrecht et al. |

(Continued)

FOREIGN PATENT DOCUMENTS

| CN | 101627894 A | 1/2010 |
|---|---|---|
| KR | 101525126 B1 | 6/2015 |

(Continued)

OTHER PUBLICATIONS

International Search Report and Written Opinion for Application No. PCT/US2017/041782, dated Oct. 20, 2017, 13 pages.

(Continued)

*Primary Examiner* — Wade Miles
*Assistant Examiner* — Bridget E. Rabaglia
(74) *Attorney, Agent, or Firm* — Schwegman Lundberg & Woessner, P.A.

(57) ABSTRACT

An instrument guide is removably inserted into a proximal portion of a cannula and extends to a distal end of the cannula to guide and support multiple surgical instruments within the cannula. The instrument guide is designed to be manufactured by injection molding of plastic material. The instrument guide includes a tube and several radial walls connected to the tube to form passageways within the tube. The radial walls are joined to a core where they intersect. The tube and radial walls have substantially the same wall thickness and the core has a minimum diameter that is substantially larger than the wall thickness to facilitate delivery of plastic material. Portions of the tube and radial walls are thinner than the general wall and rib thickness to form guideways that support surgical instruments within the passageways. Channels may be formed on an outside of the tube to deliver insufflation gas.

20 Claims, 6 Drawing Sheets

(52) U.S. Cl.
CPC .... *B29C 45/26* (2013.01); *A61B 2017/00526* (2013.01); *A61B 2017/3445* (2013.01)

(58) Field of Classification Search
CPC ............ A61B 17/3417; A61B 17/3423; A61B 17/3474; A61B 17/34; A61M 27/00; A61M 25/0026; A61M 2025/0036; A61M 2025/004; A61M 2025/006
See application file for complete search history.

(56) References Cited

U.S. PATENT DOCUMENTS

| | | |
|---|---|---|
| 2010/0004599 A1 | 1/2010 | Zhou et al. |
| 2011/0201883 A1* | 8/2011 | Cooper .............. A61B 17/3421 600/206 |
| 2014/0276947 A1 | 9/2014 | Lambrecht et al. |

FOREIGN PATENT DOCUMENTS

| | | | | |
|---|---|---|---|---|
| WO | WO-2011100125 A1 * | 8/2011 | ......... | A61B 1/00064 |
| WO | WO-2014144771 A1 | 9/2014 | | |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

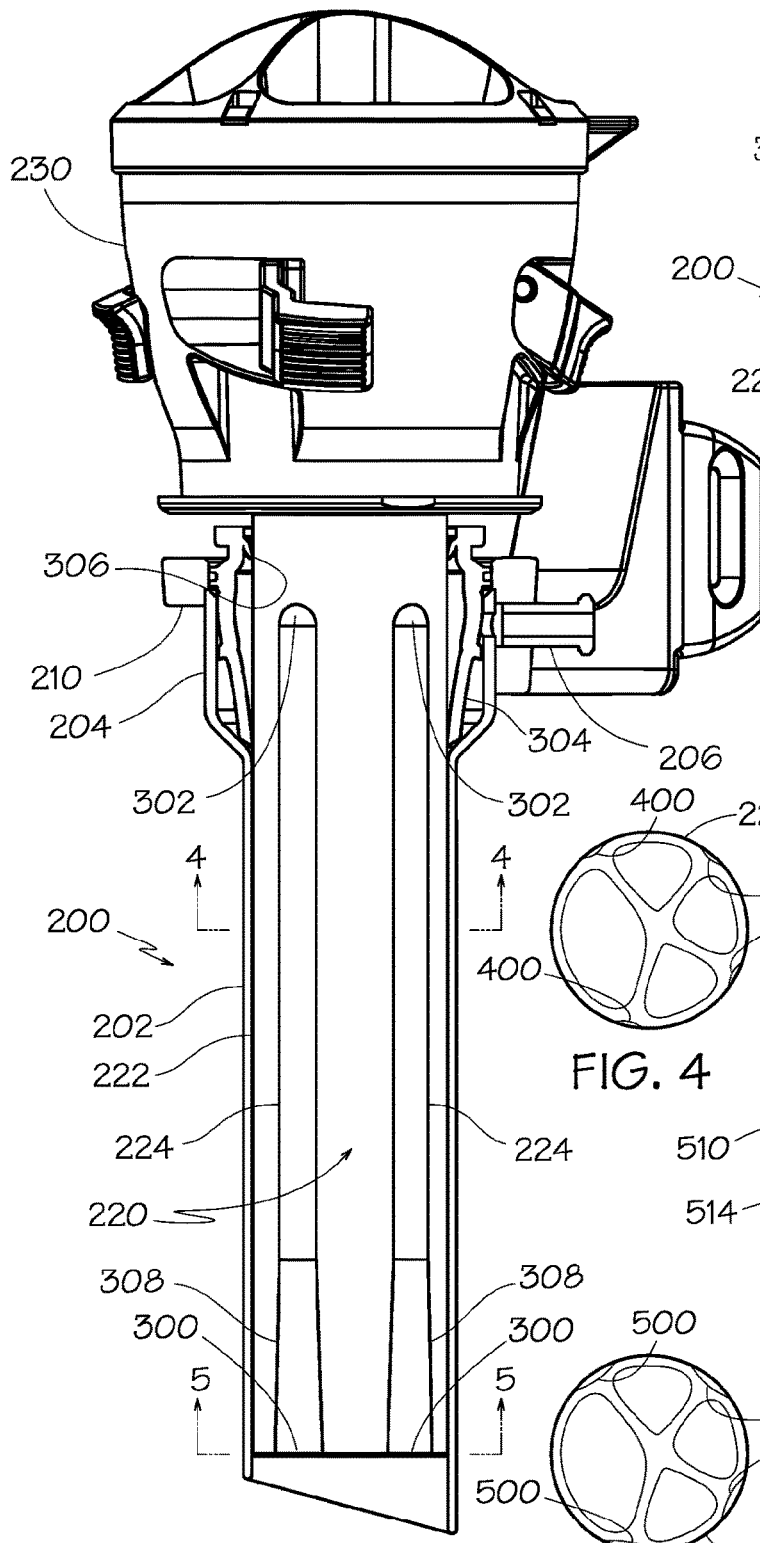
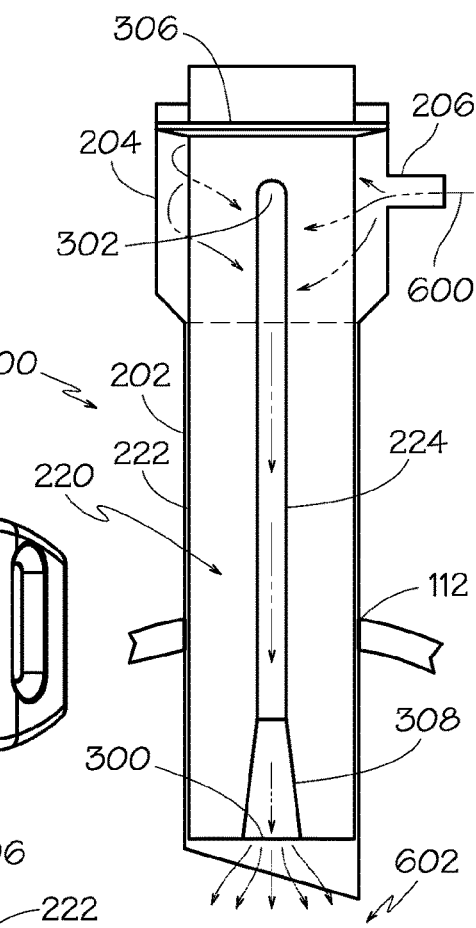
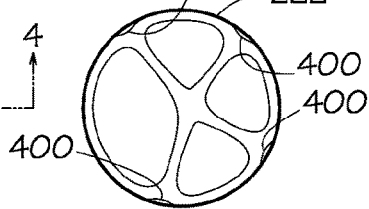
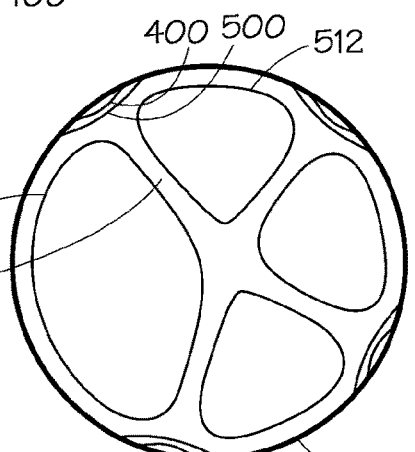

SURGICAL INSTRUMENT GUIDE

CROSS REFERENCE TO RELATED APPLICATIONS

This application is a U.S. National Stage Filing under 35 U.S.C. 371 from International Application No. PCT/US2017/041782, filed on 12 Jul. 2017, and published as WO 2018/013730 A2 on 18 Jan. 2018, which claims the benefit pursuant to 35 U.S.C. 119(e) of U.S. Provisional Application No. 62/361,934, filed 13 Jul. 2016, each of which application is specifically incorporated herein, in its entirety, by reference.

BACKGROUND

Field

Embodiments of the invention relate to the field of endoscopic surgical instruments and, in particular, to instrument guides for endoscopic surgical instruments that are suited for manufacturing methods such as by injection molding of plastic.

Background

Minimally invasive medical techniques have been used to reduce the amount of extraneous tissue which may be damaged during diagnostic or surgical procedures, thereby reducing patient recovery time, discomfort, and deleterious side effects. Traditional forms of minimally invasive surgery include endoscopy. One of the more common forms of endoscopy is laparoscopy, which is minimally invasive inspection or surgery within the abdominal cavity. In traditional laparoscopic surgery, a patient's abdominal cavity is insufflated with gas, and cannula sleeves are passed through small (approximately 12 mm) incisions in the musculature of the patient's abdomen to provide entry ports through which laparoscopic surgical instruments can be passed in a sealed fashion.

The laparoscopic surgical instruments generally include a laparoscope for viewing the surgical field and surgical instruments having end effectors. Typical surgical tools include clamps, graspers, scissors, staplers, and needle holders, for example. The surgical instruments are similar to those used in conventional (open) surgery, except that the end effector of each surgical instrument is separated from its handle by an approximately 30 cm. long extension tube, for example, so as to permit the operator to introduce the end effector to the surgical site and to control movement of the end effector relative to the surgical site from outside a patient's body.

To reduce the trauma of minimally invasive surgery even further, techniques are being developed to allow minimally invasive surgery using only a single access port into the body, such as a single incision or single natural body orifice. This access may be accomplished by using a somewhat larger cannula that can accommodate all of the instruments required for the surgery. Minimally invasive surgery performed through a single incision or natural orifice may be referred to as single port access (SPA) surgery. The single cannula that provides the single port may be introduced through a body orifice or through an incision.

If multiple surgical instruments and/or camera instruments are introduced to a surgical site through a single cannula, an instrument guide may be inserted into the cannula to support and guide the instruments within the cannula. It is desirable to use as small a cannula as possible, consistent with the size of the instruments to be passed through the cannula. Therefore, it is desirable to make the walls of the instrument guide thin.

Equipment that is introduced to a surgical site must be sterile. Sterilization of surgical equipment for reuse is expensive and it is difficult to ensure a consistent effectiveness of the procedures. Using inexpensive single use equipment eliminates the need for sterilization in the field.

Plastic parts can be produced inexpensively by injection molding. However, a part must be designed to meet a variety of constraints to be suitable for production by injection molding because it is necessary to be able to fill a mold with heated plastic material that flows into the mold. One constraint is that all areas of the part should be of substantially the same thickness to avoid deformations such as shrinkage, warp, surface irregularities, or other inaccuracies that might make the part non-functional. Another constraint is that thin walls have to be limited in length because of the tendency of the plastic material to harden quickly within a thin wall. And, any necessary transitions from one thickness to another should be carefully designed to minimize internal stress in the cooled part. But because of functional requirements, the required length of an instrument guide is difficult to achieve without making the walls of the guide thick, and so would require a cannula with a relatively larger inner diameter and correspondingly a relatively larger incision.

It would be desirable to have an instrument guide that is designed to have both sufficient length and thin walls while being capable of production by a manufacturing method such as injection molding of plastic material.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements:

FIG. 3 is a side view of assembled access port with a portion of the cannula cut away to show the instrument guide that is inserted into the cannula.

FIG. 4 is a cross-section of the instrument guide taken along line 4-4 in FIG. 3.

FIG. 5A is a cross-section of the instrument guide taken along line 5-5 in FIG. 3.

FIG. 5B is an enlarged cross-section of the instrument guide taken along line 5-5 in FIG. 3.

FIG. 6 is a schematic side view of the instrument guide inserted into the cannula to illustrate the flow of insufflation gas.

DESCRIPTION OF EMBODIMENTS

Figure 1:
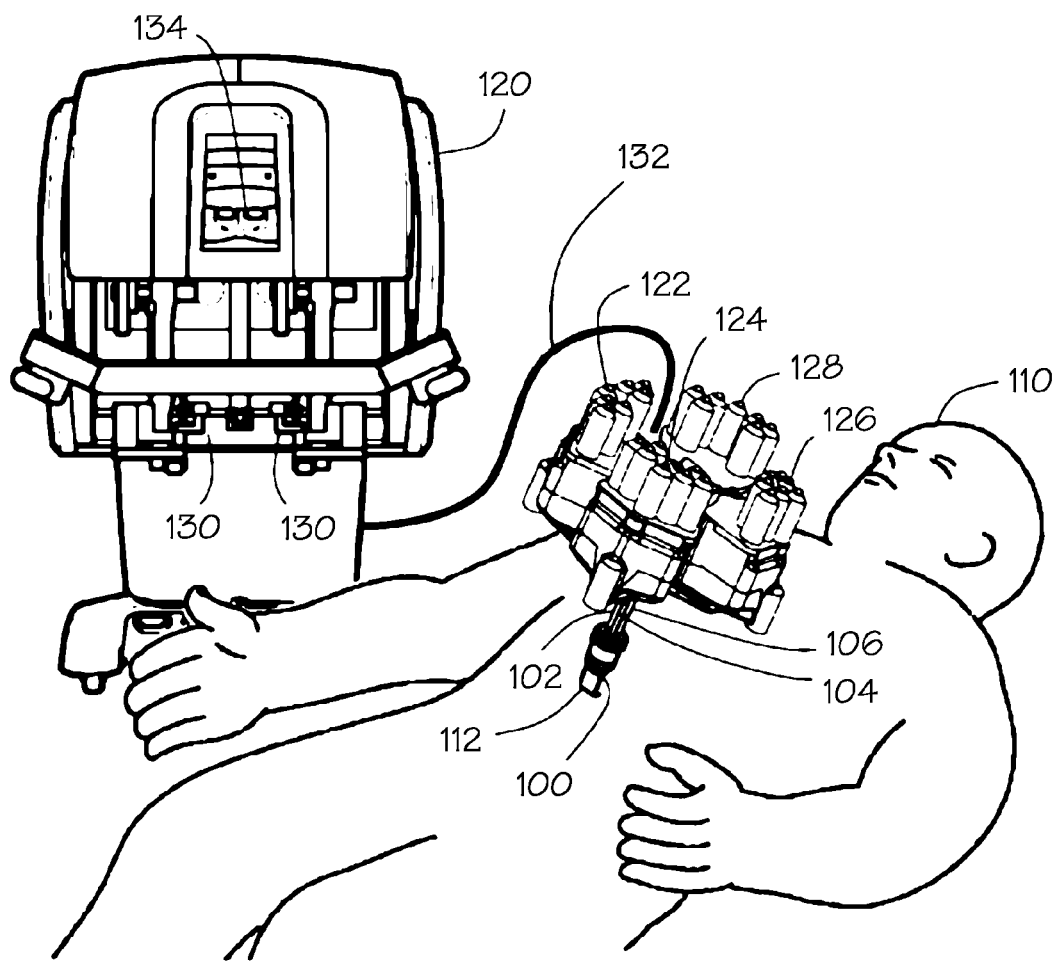
FIG. 1 is a view of an illustrative teleoperated surgical system.

In the following description, numerous specific details are set forth. However, it is understood that embodiments of the invention may be practiced without these specific details. In other instances, well-known circuits, structures, and techniques have not been shown in detail in order not to obscure the understanding of this description.

In the following description, reference is made to the accompanying drawings, which illustrate several embodiments of the present invention. It is understood that other embodiments may be utilized, and mechanical compositional, structural, electrical, and operational changes may be made without departing from the spirit and scope of the present disclosure. The following detailed description is not to be taken in a limiting sense, and the scope of the embodiments of the present invention is defined only by the claims of the issued patent.

The terminology used herein is for the purpose of describing particular embodiments only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a," "an," and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The term "object" generally refers to a component or group of components. For example, an object may refer to either a pocket or a boss of a disk within the specification or claims. Throughout the specification and claims, the terms "object," "component," "portion," "part" and "piece" are used interchangeably.

The terms "or" and "and/or" as used herein are to be interpreted as inclusive or meaning any one or any combination. Therefore, "A, B, or C" or "A, B, and/or C" mean "any of the following: A; B; C; A and B; A and C; B and C; A, B, and C." An exception to this definition will occur only when a combination of elements, functions, steps, or acts are in some way inherently mutually exclusive.

Terms of approximation, such as "substantially" and "about," as used herein are to be interpreted as meaning equal to a stated amount within a tolerance that is appropriate to the manufacturing processes that produces the stated amount or to the use or requirement for the stated amount. Thus a length that is substantially a stated amount could be the stated amount plus or minus a small amount if the length is produced by a precise process or represents a critical dimension. Conversely, a length that is substantially a stated amount could be the stated amount plus or minus a large amount if the length is produced by an imprecise process or represents a non-critical dimension.

The terms "instrument" and "surgical instrument" are used herein to describe a medical device configured to be inserted into a patient's body and used to carry out surgical or diagnostic procedures. The surgical instrument typically includes an end effector associated with one or more surgical tasks, such as a forceps, a needle driver, a shears, a bipolar cauterizer, a tissue stabilizer or retractor, a clip applier, an anastomosis device, an imaging device (e.g., an endoscope or ultrasound probe), and the like. Some instruments used with embodiments of the invention further provide an articulated support (sometimes referred to as a "wrist") for the surgical tool so that the position and orientation of the surgical tool can be manipulated with one or more mechanical degrees of freedom in relation to the instrument's shaft. Further, many surgical end effectors include a functional mechanical degree of freedom, such as jaws that open or close, or a knife that translates along a path. Surgical instruments may also contain stored (e.g., on a semiconductor memory inside the instrument) information that may be permanent or may be updatable by the surgical system. Accordingly, the system may provide for either one-way or two-way information communication between the instrument and one or more system components.

FIG. 1 shows a pictorial view of a minimally invasive teleoperated surgical procedure on a patient 110 using a single access port 100 for teleoperated surgical instruments 102, 104, 106. The single access port 100 is inserted through a single incision 112. Typically three or four surgical instruments (instruments 102, 104, and 106 are illustrated), including a camera instrument, are introduced through the single access port 100. In addition, there will generally be provisions for introducing an insufflation gas, such as carbon dioxide ($CO_2$), at or near the single access port 100. It will be appreciated that single port surgery uses a substantial amount of equipment located in a small amount of space.

The teleoperated surgical instruments 102, 104, and 106, which may include a camera instrument that may provide images of the surgical site and other instruments at the surgical site, are each coupled to a corresponding actuator, such as one of actuators 122, 124, 126, and 128. The actuators 122, 124, 126, and 128 are servo actuators that allow a surgeon to manipulate the surgical instruments using a computer-mediated control station 120. These manipulations may include functions such as changing the position and orientation of the surgical instrument's end effector (to include a camera) and operating the end effector (such as closing jaws to effect grasping, cutting, etc.). Such actuator control of surgical instruments may be referred to by various terms, such as teleoperated surgery. The actuators 122, 124, 126, and 128 may be supported on a separate structural arm that, once positioned, can be fixed relative to the patient 110. In various implementations the supporting arm may be manually positioned, may be positioned by the surgeon, or may be automatically positioned by the system as the surgeon moves one or more of the surgical instruments.

A control system couples a computer-mediated control station 120 to the teleoperated actuators 122, 124, 126, and 128. Here "computer" broadly encompasses a data processing unit that incorporates a memory and an additive or logical function, such as an arithmetic logic unit, that is programmable to perform arithmetic or logical operations. The control system may coordinate movement of the input devices with the movement of their associated surgical instruments so that the images of the surgical instruments 102, 104, 106, as displayed to the surgeon, appear at least substantially connected to the input devices in the hands of the surgeon. Further levels of connection will also often be provided to enhance the surgeon's dexterity and ease of use of the surgical instruments 102, 104, and 106.

The computer-mediated control station 120 may provide hand operated master controllers 130 that allow manipulation of the teleoperated surgical instruments 102, 104, 106 by transmitting signals, such as electrical or optical control signals provided by cables 132, to the actuators 122, 124, 126, and 128 that control the actions of the coupled surgical instruments 102, 104, and 106. Typically one of the surgical instruments, surgical instrument 102 for example, will be a camera instrument that is manipulated to place the remaining surgical instruments and the objects being manipulated within a field of view of the camera. The camera instrument transmits signals to the control station 120 so that an image captured by the camera of the instruments and objects within the field of view can be displayed on a visual display 134 that is viewed by the surgeon as the coupled surgical instruments 104, 106 are manipulated. The hand-operated controllers 130 and the visual display 134 may be arranged to provide an intuitive control of the surgical instruments 104, 106, in which the instruments move in a manner similar to the operator's hand movements with the controllers.

Figure 2:
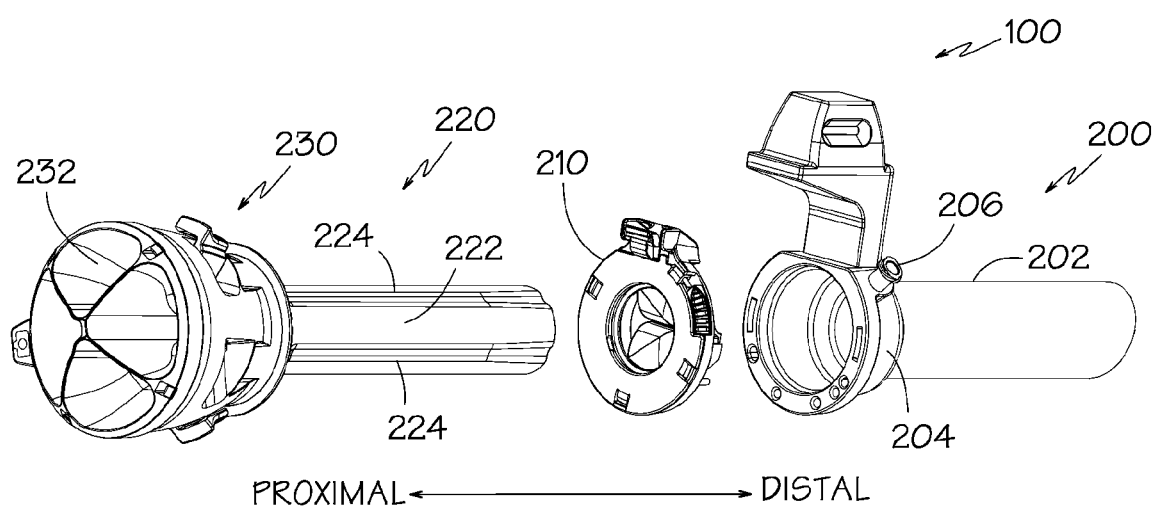
FIG. 2 is a pictorial view of an unassembled access port.

FIG. 2 is a pictorial view of an unassembled cannula and instrument guide assembly that forms an access port 100 which can be inserted through the incision 112. The access port 100 is shown before the parts are assembled into the configuration used during a surgical procedure. When assembled, the cannula and instrument guide assembly provides the single port access shown in FIG. 1.

The access port 100 includes a cannula 200 having a lumen 202 that is inserted through the incision 112 to separate and protect the incision. The access port 100 further includes an instrument guide 220 that is inserted into the cannula 200. The instrument guide 220 may be coupled to the cannula 200 in various ways to retain the instrument guide in the cannula during the surgical procedure. The instrument guide 220 guides one or more instruments through the cannula 200 to facilitate instrument access to the surgical site.

The cannula 200 includes a proximal portion 204 having an insufflation port 206 and a lumen 202 coupled to the proximal portion. The insufflation port 206 receives an insufflation gas, such as carbon dioxide ($CO_2$), that is introduced to the surgical site through the lumen 202 portion of the cannula 200.

The access port 100 may include a seal assembly 210 that is coupled to the cannula 200. The seal assembly 210 seals the access port 100 to reduce loss of insufflation gas when the instrument guide 220 is not inserted into the cannula 200.

The instrument guide 220 may be joined to a funnel assembly 230 that provides instrument receivers 232 to guide instruments into passages in the instrument guide at the proximal end of the instrument guide. The funnel assembly 230 may include seals that seal the instrument passages in the instrument guide 220 to reduce loss of insufflation gas when an instrument is not inserted into an instrument passage. The instrument guide 220 may include one or more instrument passages. Instrument guides may include one, two, three, four, five, six, or more instrument passages. The instrument passages may all be the same size and shape or they may vary in size and/or shape. Each instrument passage may have a circular cross-section or an oval cross-section or other cross-section shape that corresponds to the shape of the instrument shaft to be supported by the instrument passage.

The distal portion of the instrument guide 220 is configured to fit closely within the lumen 202 portion of the cannula 200. Each of the one or more instrument passages in the instrument guide 220 is configured to support a single surgical instrument at a defined position within the cannula 200. The surgical instruments are inserted into the access port 100 through the instrument receivers 232 in the funnel assembly 230 so that they are directed into the instrument passages at a proximal end of the instrument guide 220. The surgical instruments are supported by the instrument passages until they emerge from a distal end of the instrument guide 220. In some embodiments, the instrument guide 220 may be formed from an electrically non-conductive material to aid in electrically isolating the instruments, which may carry an electrical charge used for electrosurgical applications (e.g., cauterization). In other embodiments, the instrument guide 220 may be formed from a conductive material, such as metal or conductive plastic, to aid in dissipating any electrical charge that might build up on the instruments passing through the guide.

In some embodiments, the cannula 200 may be reusable (e.g., after cleaning and sterilization). Some or all of the instrument guide 220, the funnel assembly 230, and the seal assembly 210 may be provided as a sterile, disposable kit, e.g., a gamma sterilized kit, so that a new instrument guide, a new funnel assembly, and/or a new seal assembly may be used for each surgical procedure.

FIG. 3 shows a side view of the access port 100 with the cannula 200 cut away along a diameter to show the instrument guide 220 inserted into the cannula. The instrument guide 220 includes at least one channel 224 on an outer surface 222 of an outer wall of the instrument guide to form a passage for insufflation gas from the insufflation port 206 to the distal end of the lumen 202 portion of the cannula 200.

The channel 224 is adjacent an interior surface of the lumen 202 to form the passage for insufflation gas when the instrument guide 220 is inserted into the lumen. The channel 224 extends completely to the distal end 300 of the instrument guide 220. The channel 224 extends toward but does not reach the proximal end of the instrument guide 220. The channel 224 extends toward the proximal end sufficiently for the proximal end 302 of the channel to receive insufflation gas that flows from the insufflation port 206 and through the proximal portion 204 of the cannula 200.

The seal assembly 210 may include a proximal seal 306 and sealing flaps 304. The proximal seal 306 seals the instrument guide 220 beyond the proximal end 302 of the channels 224 to prevent insufflation gas from escaping past the instrument guide at the proximal end of the cannula 200. The sealing flaps 304 are opened when the instrument guide 220 is inserted into the lumen 202. While the sealing flaps 304 appear to block the flow of insufflation gas from the insufflation port 206 to the proximal end 302 of the channels, there are openings between the flaps that allow the flow of insufflation gas throughout the proximal portion 204 of the cannula 200. Thus the cannula and instrument guide assembly of the access port 100 provides a mechanism for introducing insufflation gas into the surgical sites while minimizing the loss of insufflation gas from the assembly.

FIG. 4 is a cross-section of the instrument guide 220 taken along section line 4-4. FIGS. 5A and 5B are cross-sections of the instrument guide 220 taken along section line 5-5. FIG. 5A omits the detail of the channel end view that is shown in the enlarged view of FIG. 5B.

It is necessary to provide a flow rate of insufflation gas sufficient to inflate the surgical region to a set pressure, perhaps 8 to 14 mm Hg, and replace gas loss due to leakage. Insufflation gas may be supplied at a pressure of about 15 mm Hg (about 2,000 Pa). The flow rate may be about 20 l/min. It will be appreciated that the velocity of insufflation gas flowing through the one or more channels 224 depends on the cross-sectional area of the channel. The flow will have a higher velocity when the cross-sectional area is small and a lower velocity when the cross-sectional area is large. But it is desirable to have a small cross-sectional area for the one or more channels 224 to minimize the diameter of the instrument guide 220 and the cannula's lumen 202. The cross-sectional area for the one or more channels 224 is constrained by the need to maintain a certain wall thickness for the structural integrity and manufacturability of the instrument guide 220.

It is also desirable to avoid high velocity flow of insufflation gas that can disturb or even damage tissues adjacent the distal end of the cannula 200 where the insufflation gas is discharged into the surgical site. To provide a small diameter instrument guide 220 while minimizing the discharge velocity of insufflation gas, the one or more channels 224 having a first cross-sectional area at a proximal end of the channel and a second cross-sectional area at a distal end of the channel that is larger than the first cross-sectional area.

The one or more channels 224 have the first cross-sectional area for the majority of the length of the channel. A transitional section 308 begins close to the distal end of the channel 224 to provide a transition to the second cross-sectional area. The transition is made just long enough to avoid introducing turbulence in the flow of the insufflation gas. In some embodiments, the transition from the first cross-sectional area to the second cross-sectional area is about 1 inch (about 25 mm) long. By limiting the larger cross-sectional areas to the distal end 300 of the instrument guide 220, the adverse consequences of the larger cross-sectional areas are minimized. This allows the instrument guide 220 to have a smaller diameter than would be possible if the channel 224 had the second cross-sectional area for its entire length. In some embodiments, the second cross-sectional area is at least twice the first cross-sectional area, reducing the discharge velocity of the insufflation gas to half or less than the velocity at the proximal end of the channel. For example, in one embodiment the first cross-sectional area is about 0.0023 in$^2$ (1.5 mm$^2$) and the second cross-sectional area is about 0.0050 in$^2$ (3.0 mm$^2$).

The one or more channels 224 are located relative to the interior passageways to provide a first wall thickness for the instrument guide where the channel has the first cross-sectional area and a second wall thickness for the instrument guide where the at least one channel has the second cross-sectional area, the second wall thickness being less than the first wall thickness.

FIG. 6 shows a schematic side view of the instrument guide 220 inserted into the cannula 200 to illustrate the flow of insufflation gas from the insufflation port 206 to the surgical site 602. The double dashed arrows suggest the flow of insufflation gas 600. The cannula 200 is inserted through an incision 112 which seals against the outside of the cannula. The proximal portion 204 of the cannula 200 forms a plenum that supplies insufflation gas. The proximal portion 204 is sealed at the proximal end by the proximal seal 306 sealing against the instrument guide 220.

Insufflation gas enters the one or more channels 224 on the outer surface 222 of the instrument guide 220 from the plenum formed by the proximal portion 204 of the cannula 200 and flows toward the distal end 300 of the instrument guide. The one or more channels 224 include a transition section 308 that has an increasing cross-sectional area at the distal end 300 of the channels. As suggested by the reduced length of the double dashed arrow in the transition section 308, the increasing cross-sectional area of the transition section reduces the velocity of the insufflation gas before it is discharged into the surgical site 602.

The instrument guide may be manufactured by injection molding of a plastic resin. As is well known in the plastic molding industry, there are numerous design guidelines that must be considered to design a part that can be successfully manufactured by an injection molding process. Many of these guidelines are based on the need to cause the plastic resin to fill the mold when the heated plastic resin is forced into the mold under pressure.

One guideline for injection molding limits the length of thin sections so that the plastic resin does not harden excessively before reaching the end of the thin section. A desirable plastic for manufacturing an instrument guide is a polycarbonate resin, such as Calibre™ Megarad™ 2081-15 polycarbonate resin from Trinseo S.A., because of its dimensional stability and durability. The length of a thin wall manufactured from injection molded polycarbonate resin is limited to less than one hundred times the thickness of the wall. An instrument guide may be about 5 inches (about 125 mm) in length and thus require the use of wall thicknesses of 0.050 inches (1.25 mm) or greater. This thickness is difficult to provide in an instrument guide having an outside diameter of less than 1 inch (25.4 mm) and having passages for four instruments, one of which is a camera, a typical requirement for an instrument guide.

FIGS. 7 through 10 are cross-sections of an exemplary instrument guide taken along the same section line 4-4 as the cross-section shown in FIG. 4, illustrating a design process for designing an instrument guide to be manufactured by an injection molding process. These cross-sections could also be applied to the embodiments already described.

Figure 7:
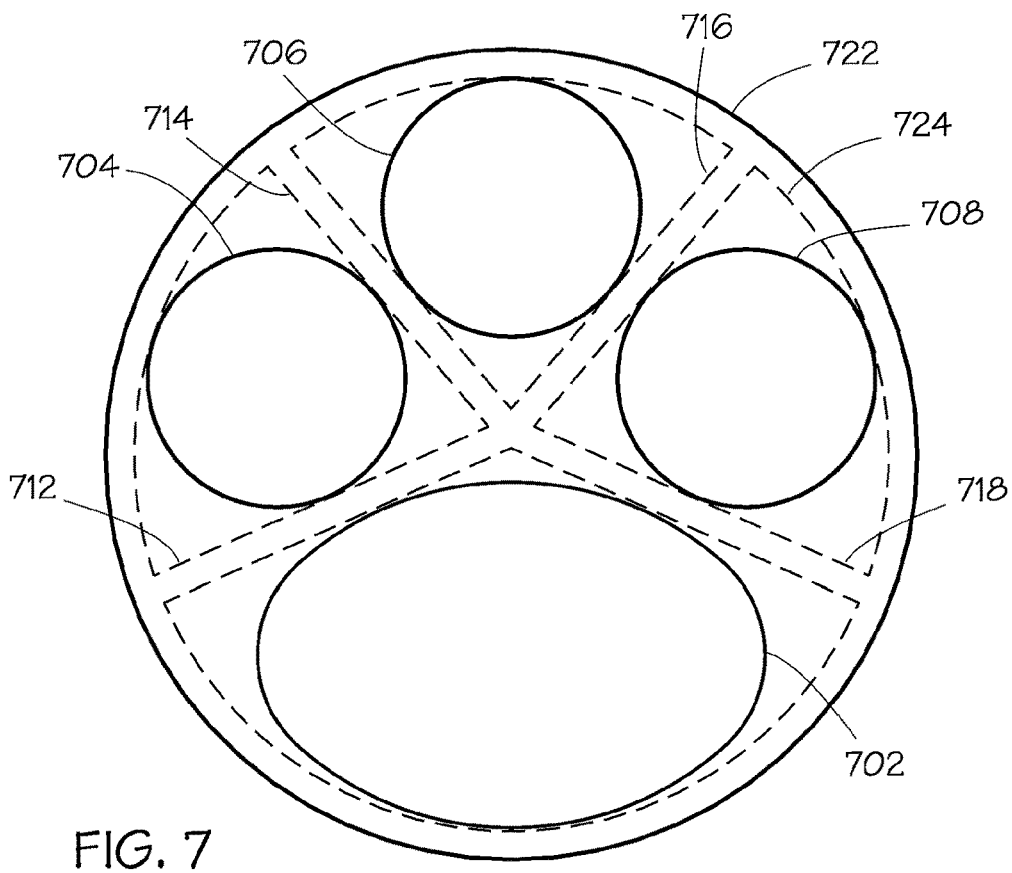
FIG. 7 shows a cross-section of the outside surfaces of a camera instrument and three additional surgical instruments and the outside surface of the instrument guide.

FIG. 7 shows a cross-section of the outside surfaces of a camera instrument 702 and three additional surgical instruments 704, 706, 708 and the outside surface 722 of the instrument guide. As illustrated, the camera instrument has an oval cross section, and the three additional instruments have round cross sections. The camera instrument 702 and the three additional surgical instruments 704, 706, 708 are placed within the outside surface 722 of the instrument guide such that the minimum space between adjacent instruments is substantially the same, as suggested by the model radial walls 712, 714, 716, 718 drawn with dashed lines. Likewise, the minimum space between the outside surface 722 of the instrument guide and the adjacent instruments 702, 704, 706, 708 is substantially the same as the radial wall separation as suggested by the model outer wall between outside surface 722 and circular dashed line 724.

To ensure the desired tight (ideally, tightest possible) packing within the cannula, the instruments may be placed using analytic techniques or by iterative graphical methods, which may be more effective when instruments of differing geometries, such as the camera instrument 702, are being placed. The camera instrument 702 may house a stereoscopic camera, such as the one disclosed in U.S. Pat. No. 8,556,807 B2 (filed May 15, 2010), that requires the outside surface of the camera instrument to have a generally oval shape. The outside surface of the camera instrument may be in the form of a four circular curve approximation to an ellipse. The use of circular curve segments to form the outside surface of the camera instrument may simplify construction of the camera instrument and/or the instrument guide.

In one exemplary embodiment of an instrument guide, the outside surface of the instrument guide has a diameter of about 1 inch (about 2.54 centimeters) and it is about 5 inches (about 12.7 centimeters) in length. The larger curved surfaces of the exemplary camera instrument have a radius of about 0.4 inches. The remaining surgical instruments are about 0.3 inches in diameter. The minimum space between adjacent instruments and between the outside surface of the instrument guide and the adjacent instruments is about 0.03 of an inch. It will be appreciated that the exemplary instrument guide cannot be injected molded from a polycarbonate resin with walls this thin because of the length of the guide.

Figure 8:
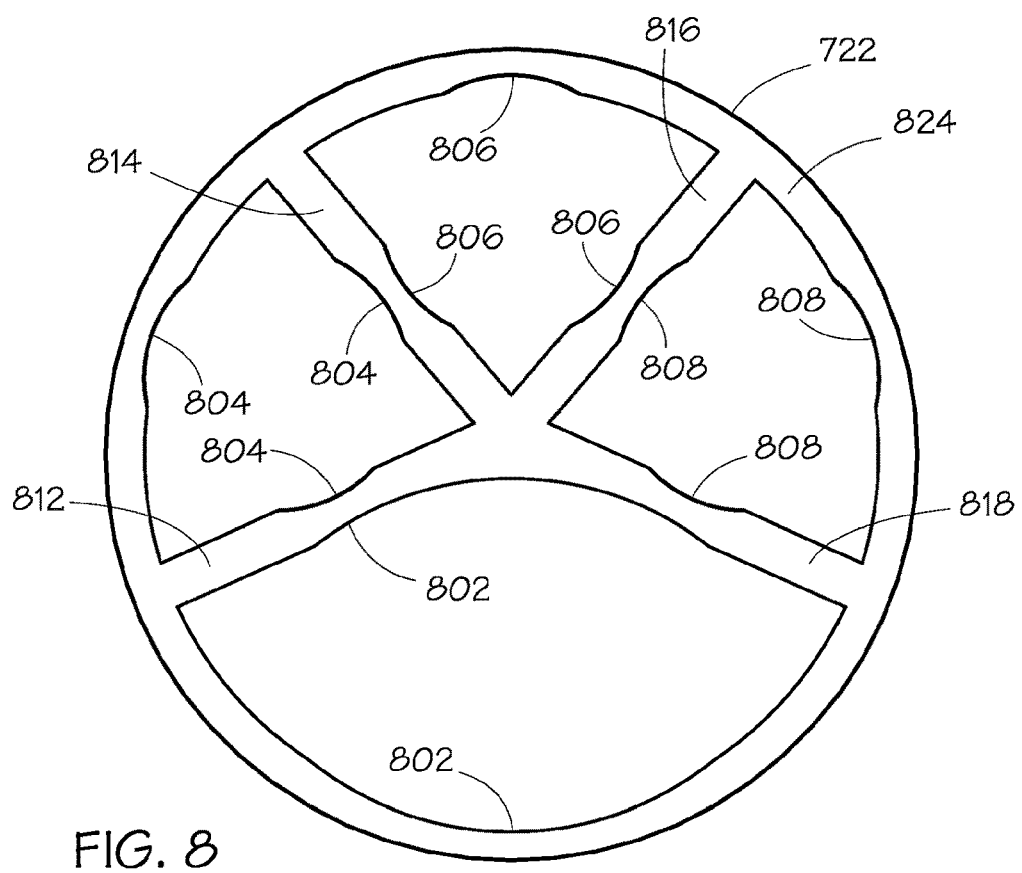
FIG. 8 shows a cross-section of an instrument guide in which wall thicknesses have been increased.

FIG. 8 shows a cross-section of an instrument guide in which the radial walls 812, 814, 816, 818 and the outer wall 824 have been increased in thickness except for the areas 802, 804, 806, 808 where the placement of the instruments requires the walls to be thinner. These thinner areas form guideways 802, 804, 806, 808 for the instruments—guideways 802 for instrument 702, guideways 804 for instrument 704, guideways 806 for instrument 706, and guideways 808 for instrument 708. The radius of each of these guideways corresponds to the radius of the instrument it receives to allow a sliding fit, which may help stabilize the instruments laterally within the instrument guide and may help the instruments move more easily in an axial direction as they are inserted into and withdrawn from the instrument guide. It will be appreciated that the axial motion of the instruments in the guide may provide one axis of motion for an instrument as it is used in a surgical procedure. In the exemplary embodiment of an instrument guide, the walls 812, 814, 816, 818, 824 may be increased to a thickness of about 0.05 inches, which is sufficient for injection molding requirements, despite the relatively thinner areas at the guideways. Stated another way, the general thicknesses of each of the radial walls and the outer wall are substantially the same and are sufficient for injection molding for the lengths of the walls, but the thicknesses of the radial and outer walls in portions of the walls where a guideway is formed is less than the general thickness, and these lesser thicknesses has been found acceptable for injection molding.

It can be seen in FIG. 8 that one side of a radial wall partially defines a first passageway, and the reverse side of the radial wall partially defines a second passageway. Thus as illustrated a guideway for the first passageway is formed in one surface of a radial wall, and a second guideway for the second passageway is formed in the reverse surface of the radial wall. In the illustrated embodiment the guideways are generally opposite one another in the obverse and reverse surfaces across the wall, although in other instrument placement geometries the guideways formed in a single wall may be offset from one another across the wall.

Figure 9:
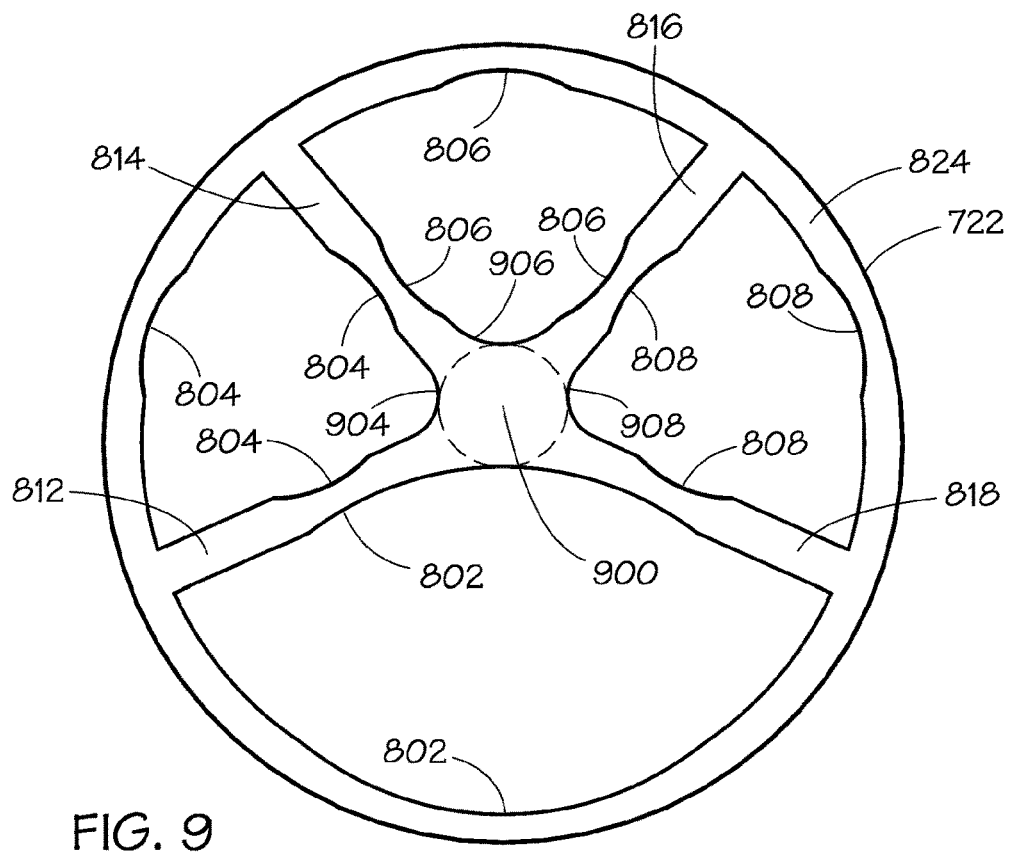
FIG. 9 shows a cross-section of the instrument guide radial walls have been joined by a radius.

FIG. 9 shows a cross section of the instrument guide in which the "V" where the radial walls 812, 814, 816, 818 intersect has been joined by a radius 904, 906, 908. In the three passageways for the surgical instruments, the instruments 704, 706, 708 do not occupy the "V" region. Therefore, it is possible to join the walls with a large radius. Preferably the joining radius is smaller than the outside radius of the surgical instruments so there is a substantial clearance between the joining radius and the instrument. The passage way for the camera instrument 702 is such that the instrument guideway 802 may be used as the joining radius rather than removing material at the intersection of the walls to provide a clearance guideway. In the exemplary embodiment of an instrument guide, the joining radii may be 0.05 to 0.10 inches.

Joining the radial walls 812, 814, 816, 818 with large radii creates a solid central core 900 that is much thicker than the radial walls and the tube's outer wall 824. While conventional design practice for injection molded parts avoids joining thick sections to thin sections because of warpage and shrinkage issues, it has been found that a thick solid central core can be used in the instrument guide because the guide is symmetrically supported by the radial walls, and the solid central core does not provide any critical surfaces in the guide. Providing a thick solid central core provides a good flow path for the plastic resin during injection molding and has been found to overcome the issues commonly associated with creating long thin walls by injection molding because the resin flows from the core outward through the radial walls and into the outer wall.

Figure 10:
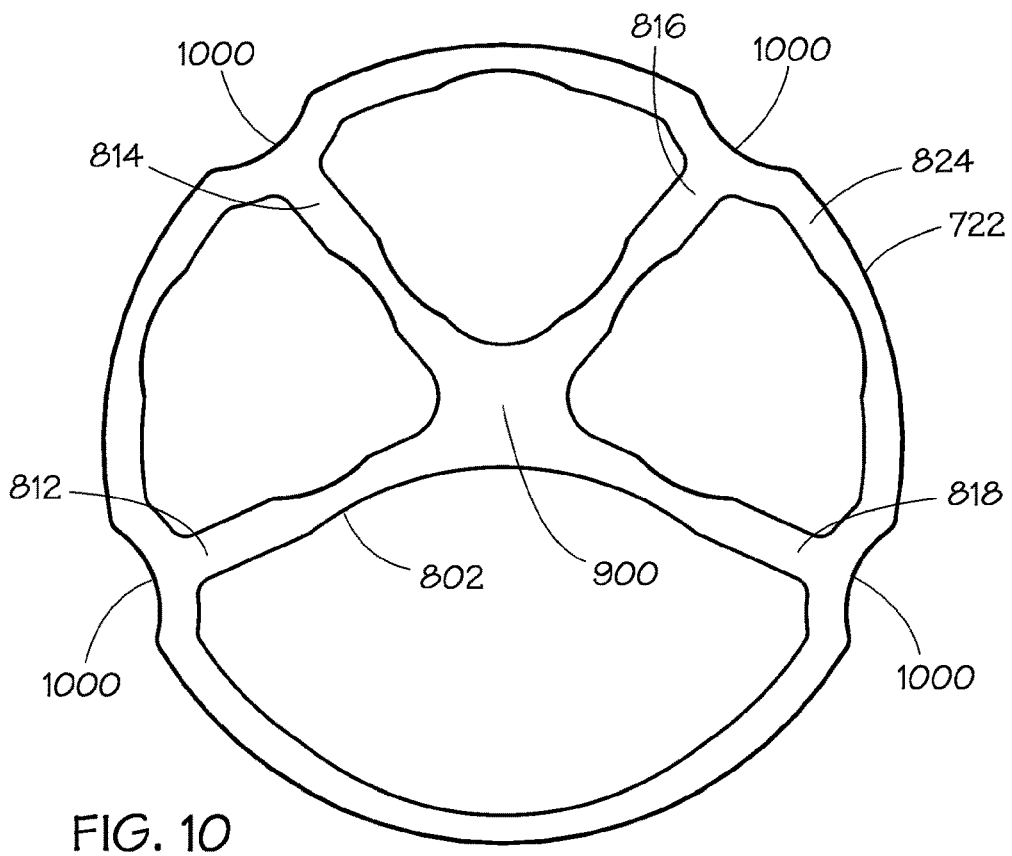
FIG. 10 shows a cross-section of the instrument guide in which channels for insufflation gas have been added to the outside surface of the instrument guide.

The central core has a minimum "diameter" that is substantially larger than the wall thickness, where "diameter" means the diameter of the largest circular cylinder that could be contained within the core. In the exemplary embodiment of an instrument guide, the central core may be larger than a cylinder with a diameter of 0.15 inches as suggested by the dashed circle shown over the core. Thus the central core may be about three times the thickness of the thickened portions of the walls and more than four times the thickness of the thinnest portions of the walls at the guideways. The core has a minimum diameter that is substantially larger than the wall thickness FIG. 10 shows a cross-section of an instrument guide in which channels 1000 for insufflation gas have been added to the outside surface 722 of the instrument guide, as described previously. The channels are formed in the outer wall and centered over the radial walls 812, 814, 816, 818. This position allows the channels to be formed without interfering with the placement of the instruments. The thickness of the outer circular wall can be kept substantially constant across the insufflation gas channels. The distal portion of the channels may be enlarged to provide a larger cross-section area as described previously. In some embodiments, a small radius is used where the radial walls meet the outer wall.

Figure 11:
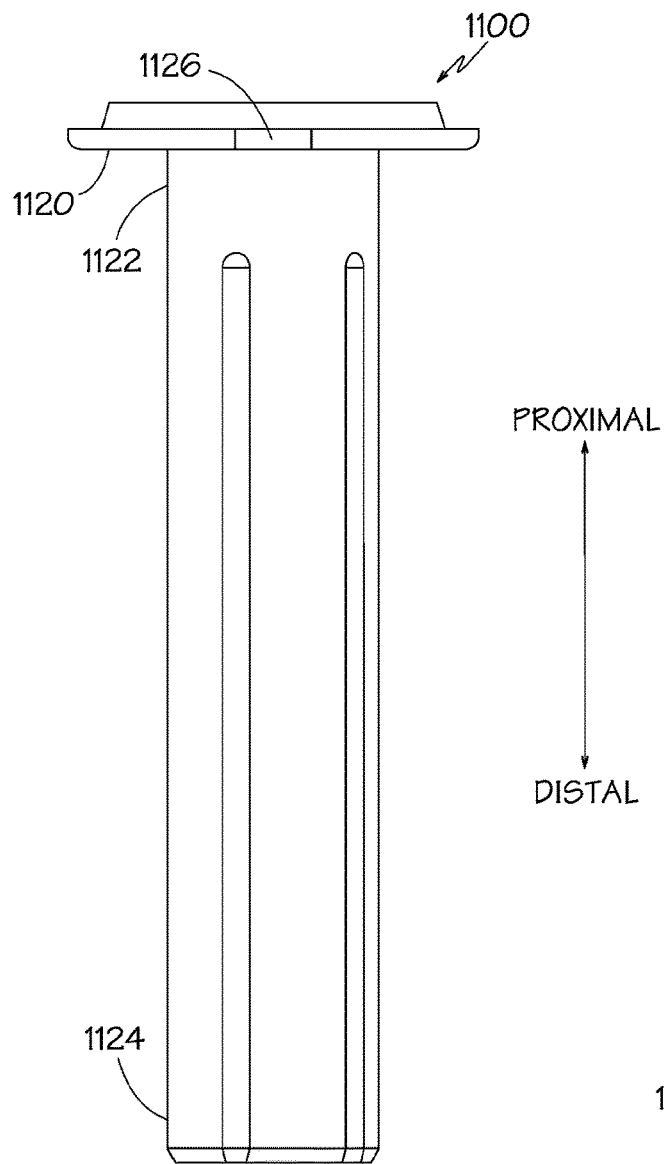
FIG. 11 shows a side view of an exemplary instrument guide.
Figure 13:
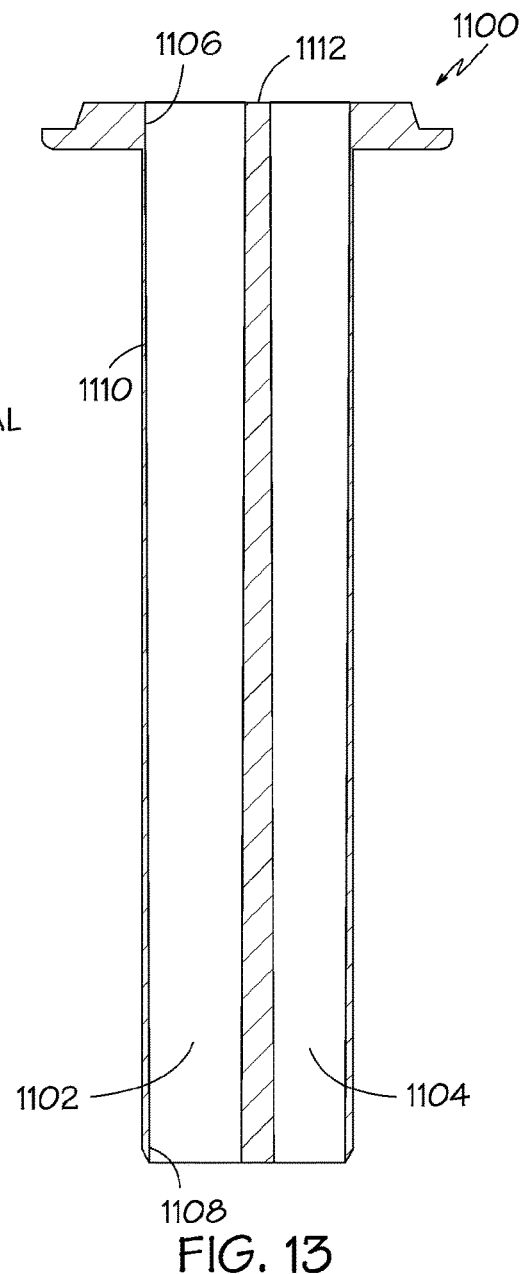
FIG. 13 shows a cross-section view of the exemplary instrument guide taken along line 13-13 in FIG. 12.
Figure 12:
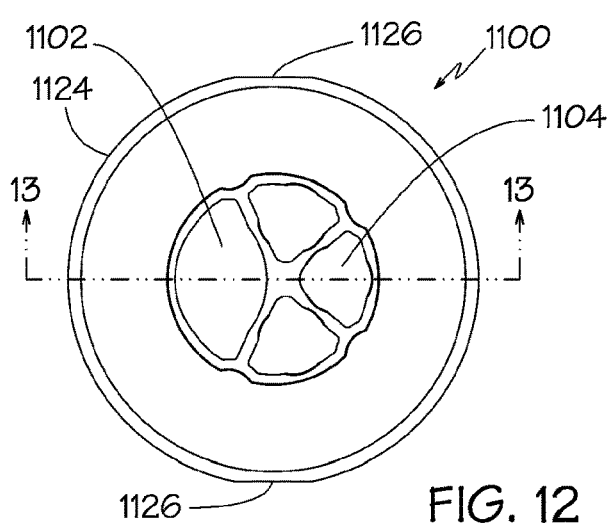
FIG. 12 shows an end view of the exemplary instrument guide of FIG. 11.
Figure 14:
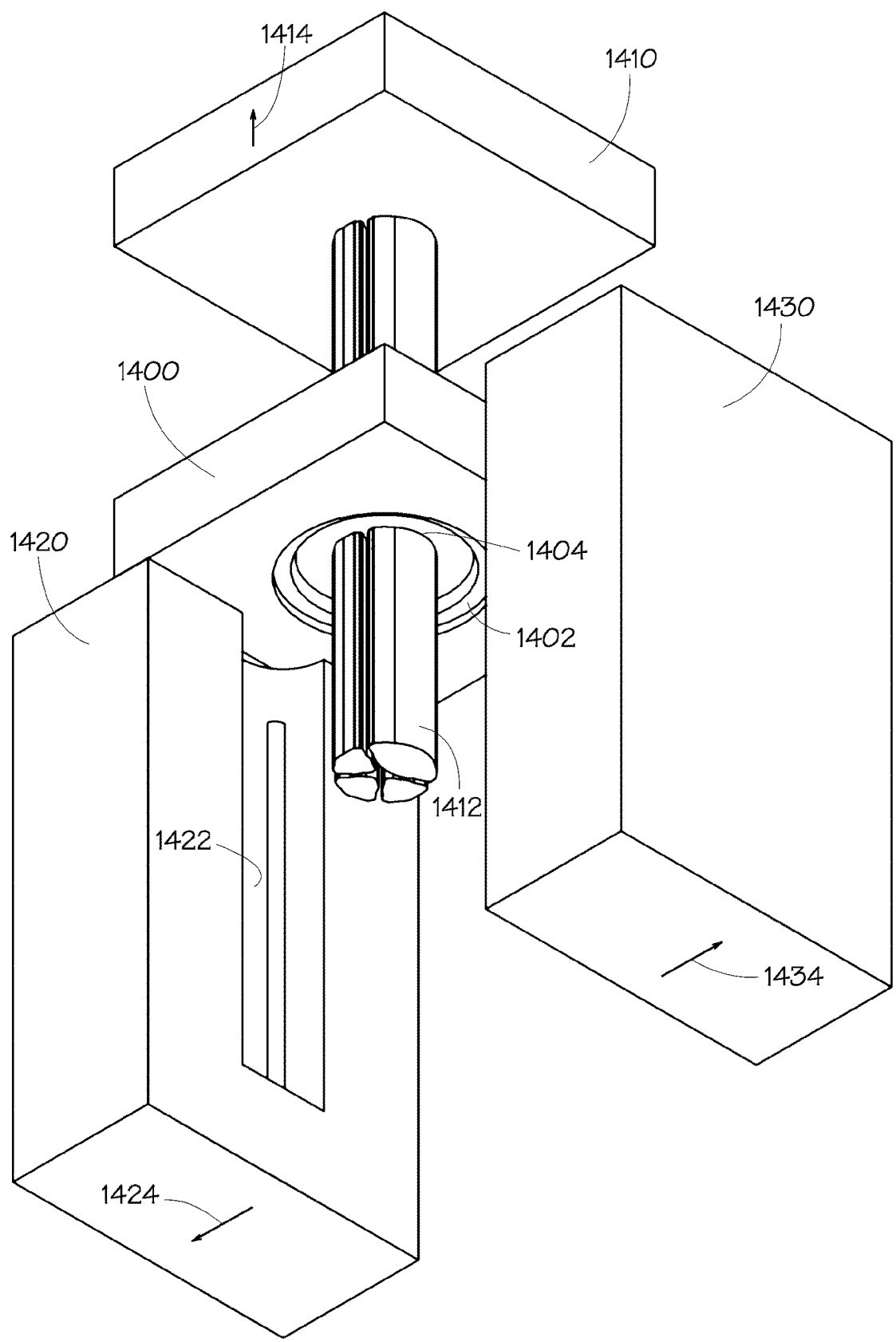
FIG. 14 shows a schematic representation of a mold that can be used to produce an instrument guide by injection molding.

FIG. 11 shows a side view of an exemplary instrument guide 1100. FIG. 12 shows an end view of the exemplary instrument guide 1100. FIG. 13 shows a cross-sectional view of the exemplary instrument guide 1100 taken along line 13-13 in FIG. 12. FIG. 14 shows a schematic representation of a mold that can be used to produce an instrument guide by injection molding.

To facilitate release of an injection molded part from the mold, surfaces are generally provided with draft, a small angle to the surface so that the part separates from the mold as the part moves out of the mold. For example, the passageways 1102, 1104 have a smaller opening 1108 at the distal end of the instrument guide and a larger opening 1106 at the proximal end. Conversely, the tube walls 1110 and the core 1112 have a thicker cross section at the distal end of the instrument guide and a thinner cross section at the proximal end. Thus the passageways 1102, 1104 will separate from the mold as the instrument guide moves in a distal direction relative to the mold. The amount of draft shown in FIG. 13 has been greatly exaggerated so that the draft can be seen. The illustrative cross section clearly shows the much greater thickness of the core 1112 relative to the tube walls 1110.

Design guidelines for injection molding recommend at least one-half degree of draft and suggest one degree or more of draft as a preferred practice. One-half degree of draft will create almost 0.1 inches (almost 2.5 millimeters) more clearance between an instrument and the guideway passage at the proximal end than at the distal end of a 5 inch (12.7 centimeter) long passageway. But, 0.1 inches (2.5 millimeters) of additional clearance at the proximal end of the passageway would allow excessive movement at the distal end of the instrument. In practice, 0.13 degrees of draft creates less than 0.03 inches (0.76 millimeters) more clearance at the proximal end and controls the position of the distal end of the instrument acceptably. Special design considerations described below are used to allow separation of the part from the mold with this small amount of draft.

The instrument guide includes a flange 1120 that extends outwardly from the proximal end 1122 of the tube. Referring to FIG. 14, the flange may be formed in a cavity 1402 of a first mold segment 1400. The passageways may be formed by a second mold segment 1410 that includes cylindrical segments 1412 that form the passageway openings and the guideways. The cylindrical segments 1412 pass through openings 1404 in the first mold segment 1400. The cylindrical segments 1412 are ejected from the molded instrument guide by moving the second mold segment 1410 away from the first mold segment 1400 in the direction suggested by the arrow 1414 on the second mold segment. The support provided by the flange 1120 in the 1402 of the first mold segment 1400 allows the cylindrical segments 1412 to be withdrawn from the instrument guide and pass through the openings 1404 in the first mold segment 1400 despite having much less than the normal amount of draft for ejecting a part from a mold.

The outside surface of the tube has the same outside diameter from the distal end 1124 to the proximal end 1122 so that the instrument guide is stably positioned within the cannula 200 (FIG. 3). This uniform outside diameter requires the use of side action mold segments 1420, 1430 that each include a cavity 1422 that forms one-half of the outside surface of the tube and the insufflation passages. The side action mold segments 1420, 1430 move away from the molded instrument guide in opposite directions from one another as suggested by the arrows 1424, 1434 on the mold segments.

It has been found that two gate sites 1126 can be placed at diametrically opposed locations on the periphery of the flange 1120 to reliably fill the instrument guide mold cavity. These locations are not dimensionally critical, and the gate site vestiges can be readily trimmed.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. For example, while the use of the channels of the instrument guide have been described for the delivery of insufflation gas to the surgical site, the same or similar channels can be used to evacuate gases and/or smoke from the surgical site. The description is thus to be regarded as illustrative instead of limiting.

The invention claimed is:

1. A medical device comprising:
    an instrument guide comprising a tube, a solid core, and a plurality of radial walls;
    the tube having a proximal end, a distal end, and an outer wall;
    the solid core extending from the proximal end to the distal end of the tube; and
    the plurality of radial walls extending from the proximal end to the distal end of the tube and from the solid core to the outer wall of the tube, each adjacent pair of the plurality of radial walls forming one of a plurality of passageways bounded by the solid core and the tube;
    wherein a thickness of the outer wall of the tube and a thickness of each individual radial wall of the plurality of radial walls are substantially the same first thickness, and the solid core has a minimum diameter that is substantially larger than the first thickness,
    wherein a first instrument guideway is formed in a surface of a first radial wall of the plurality of radial walls, and
    wherein a second thickness of the first radial wall at the first instrument guideway is less than the first thickness.

2. The medical device of claim 1,
    wherein a first instrument guideway is formed in the outer wall of the tube; and
    wherein a second thickness of the outer wall of the tube at the first instrument guideway is less than the first thickness.

3. The medical device of claim 1,
    wherein a first instrument guideway is formed in the outer wall of the tube that defines a first passageway of the plurality of passageways, and a second thickness of the outer wall of the tube at the first instrument guideway is less than the first thickness; and
    wherein a second instrument guideway is formed in a first radial wall of the plurality of radial walls that defines the first passageway, and a third thickness of the first radial wall at the second instrument guideway is less than the first thickness.

4. The medical device of claim 1, wherein each of the plurality of passageways includes three guideways, one guideway of the three guideways formed by a thin portion of the outer wall of the tube, and the remaining two guideways of the three guideways formed by a thin portion of each of the adjacent pair of the plurality of radial walls forming the plurality of passageways.

5. The medical device of claim 1,
    wherein the first radial wall of the plurality of radial walls comprises a first surface and a second surface reverse of the first surface;
    wherein the first instrument guideway is formed in the first surface and a second instrument guideway is formed in the second surface; and
    wherein the third thickness of the first radial wall between the first instrument guideway and the second instrument guideway is less than the first thickness.

6. The medical device of claim 1, wherein an outside diameter of the tube is constant from the distal end to the proximal end.

7. The medical device of claim 6, wherein the first thickness is less at the proximal end than at the distal end of the tube, causing each of the plurality of passageways to be larger at the proximal end of the tube than at the distal end of the tube.

8. The medical device of claim 7, formed by injection molding.

9. The medical device of claim 1, wherein the first instrument guideway is defined by a constant radius curve.

10. The medical device of claim 1,
    wherein an insufflation gas channel is defined in an outer surface of the outer wall of the tube; and wherein the insufflation gas channel flares outward at the distal end of the tube.

11. The medical device of claim 10, wherein the insufflation gas channel is further defined in the outer surface of the outer wall of the tube opposite a location where one of the plurality of radial walls joins the outer wall.

12. The medical device of claim 10, wherein the outer wall of the tube maintains the first thickness at the insufflation gas channel.

13. The medical device of claim 1, wherein the tube includes a plurality of insufflation gas channels formed on an outside surface of the tube, each of the plurality of insufflation gas channels extending from the distal end of the tube toward the proximal end and centered over a corresponding one of the plurality of radial walls.

14. The medical device of claim 13, wherein each of the plurality of passageways is shaped such that the thickness of the outer wall of the tube remains substantially the same at the plurality of insufflation gas channels.

15. The medical device of claim 13, wherein each of the plurality of insufflation gas channels has a larger cross-sectional area at the distal end of the tube than at the proximal end of the tube.

16. The medical device of claim 13, wherein each of the plurality of insufflation gas channels extends toward but does not reach the proximal end of the tube of the instrument guide.

17. The medical device of claim 1, further comprising a flange extending outwardly from the proximal end of the tube.

18. The medical device of claim 1, further comprising:
a cannula including a proximal portion having an insufflation port, the cannula having a lumen extending from the proximal portion of the cannula; and
the instrument guide removably inserted into the proximal portion of the cannula and extending through the cannula to a distal end of the lumen.

19. The medical device of claim 18, wherein the tube includes a plurality of insufflation gas channels adjacent an interior surface of the lumen to form a passage for insufflation gas.

20. The medical device of claim 1, further comprising:
a funnel assembly joined to the proximal end of the tube of the instrument guide, the funnel assembly comprising a plurality of funnels, each funnel of the plurality of funnels corresponding to a corresponding one of the plurality of passageways.

* * * * *